United States Patent [19]
Burczak et al.

[11] Patent Number: 5,756,298
[45] Date of Patent: May 26, 1998

[54] **OLIGONUCLEOTIDES AND METHODS FOR THE DETECTION OF *CHLAMYDIA TRACHOMATIS***

[75] Inventors: John D. Burczak, Highland Park; John J. Carrino, Gurnee; Paul A. Klonowski, Wonder Lake; Matthew T. Manlove, Vernon Hills; Ronald L. Marshall, Zion; Edward K. Pabich, Chicago, all of Ill.; John A. Salituro, Kenosha, Wis.

[73] Assignee: Abbott Laboratories, Abbott Park, Ill.

[21] Appl. No.: 708,431

[22] Filed: Sep. 5, 1996

Related U.S. Application Data

[60] Continuation of Ser. No. 449,863, Apr. 24, 1995, abandoned, which is a division of Ser. No. 116,389, Sep. 3, 1993, Pat. No. 5,601,978.

[51] Int. Cl.$^6$ .............................. C12Q 1/68; C12P 19/34; C07H 21/04
[52] U.S. Cl. .................. 435/6; 435/91.51; 536/24.33
[58] Field of Search ............... 435/6, 91.2, 91.51; 536/24.32, 24.33; 935/77, 78

[56] References Cited

U.S. PATENT DOCUMENTS

| | | | |
|---|---|---|---|
| 4,683,195 | 7/1987 | Mullis et al. | 435/91.2 |
| 5,232,829 | 8/1993 | Longiaru et al. | 435/6 |

FOREIGN PATENT DOCUMENTS

| | | |
|---|---|---|
| 0320308 | 6/1989 | European Pat. Off. . |
| 0336412 | 10/1989 | European Pat. Off. . |
| 0439182 | 7/1991 | European Pat. Off. . |
| 0546761 | 6/1993 | European Pat. Off. . |
| 8803957 | 6/1988 | WIPO . |
| 8910415 | 11/1989 | WIPO . |
| 9119812 | 12/1991 | WIPO . |
| 9204469 | 3/1992 | WIPO . |
| 9313221 | 7/1993 | WIPO . |
| 9316094 | 8/1993 | WIPO . |

OTHER PUBLICATIONS

Hatt, C., et al., "Analysis of the entire nucleotide sequence of the cryptic plasmid of *Chlamydia trachomatis* serovar L1. Evidence for involvement in DNA replication", *Nucleic Acids Research*, 16(9):4053–4067 (1988).

Baehr, W., et al., "Mapping antigenic domains expressed by *Chlamydia trachomatis* major outer membrane protein genes", *Proc. Natl. Acad. Sci.*, 85:4000–4004 (1988).

Stephens, R.S., et al., "Diversity of *Chlamydia trachomatis* Major Outer Membrane Protein Genes", *Journal of Bacteriology*, 169(9):3879–3885 (1987).

Dille, B.J., et al., "Amplification of *Chlamydia trachomatis* DNA by Ligase Chain Reaction", *Journal of Clinical Microbiology*, 31(3):729–731 (1993).

Pickett, M.A., et al., "Complete nucleotide sequence of the major outer membrane protein gene from *Chlamydia trachomatis* serovar L1", *FEMS Microbiology Letters*, 42:185–190 (1987).

Dayada, C., et al., "Complete sequence of the major outer membrane protein-encoding gene of *Chlamydia trachomatis* serovar Da*", *Gene*, 120:129–130 (1992).

Zhang, Y-X, et al., "The nucleotide sequence of major outer membrane protein gene of *Chlamydia trachomatis* serovar F", *Nucleic Acids Research*, 18(4):1061 (1989).

*Primary Examiner*—Lisa B. Arthur
*Attorney, Agent, or Firm*—Thomas D. Brainard; Paul D. Yasger

[57] ABSTRACT

The present invention relates to oligonucleotide probes useful in detecting, e.g. by hybridization or the ligase chain reaction, *Chlamydia trachomatis* DNA in the presence of other related DNA. The present invention is also directed to methods of detecting *Chlamydia trachomatis* organisms in a sample using the ligase chain reaction.

3 Claims, 2 Drawing Sheets

FIGURE 1
MOMP Regions

```
SEQ ID NO.

MOMP 435-481
1         Target      5'           GCTTTGAGTTCTGCTTCCTCCCTTGCAAGCTCTGCCTGTGGGAATCCT 3'
          Probe Set 1
2                  A  5' CZ-GCTTTGAGTTCTGCTTCCTCCCTTG
3                  A' 3' CZ-CGAAACTCAAGACGAAGGAGG
4                  B  3'                            GCTCTGCCTGTGGGAATCCT-AD 3'
5                  B' 5'                            GTTCGAGACGGACACCCGTTAGGA-AD 5'

MOMP 788-835
6         Target      5'           TTGGGATCGTTTGATGTATTCTGTACATTAGGAGCCACCAGTGGATA 3'
          Probe Set 2
7                  A  5' CZ-TTGGGATCGTTTGATGTATTCTGT
8                  A' 3' CZ-AACCCTAGCAAACTACATAAG
9                  B  3'                            TTAGGAGCCACCAGTGGATA-AD 3'
10                 B' 5'                            TGTAATCCTCGGTGGTCACCTAT-AD 5'

MOMP 1501-1546
11        Target      5'           TGGATGCAGACAAATACGCAGTTACAGTTGAGACTCGCTTGATCGA 3'
          Probe Set 3
12                 A  3' CZ-TGGATGCAGACAAATACGCAGTT
13                 A' 5' CZ-ACCTACGTCTGTTTATGCGT
14                 B  3'                            GTTGAGACTCGCTTGATCGA-AD 3'
15                 B' 5'                            TGTCAACTCTGAGCGAACTAGCT-AD 5'
```

FIGURE 2
Cryptic Plasmid Regions

SEQ ID NO.

```
    Plasmid 6917-6964
16   Target 5' GACTTTGCAACTCTTGGTGGTAGACTTGGTCATAATGGACTTTTGTTG 3'
    Probe Set 4
17    A   5' CZ-GACTTTGCAACTCTTGGTAGA
18    A'  3' CZ-CTGAAACGTTGAGAACCACCA
19    B                                    GGTCATAATGGACTTTGTTG-AD 3'
20    B'                              GAACCAGTATTACCTGAAAACAAC-AD 5'

Plasmid 6107-6160
21   Target 5' ATTTTAAGAAGACGCTTCCTTCCATTGAACTATTCTCAGCAACTTTGAATTCTG 3'
    Probe Set 5
22    A   5' B-ATTTTAAGAAGACGCTTCCTTCCATTG
23    A'  3' B-TAAAATTCTTCTGCGAAGGAAGGT
24    B                                    TATTCTCAGCAACTTTGAATTCTG-F 3'
25    B'                              TTGATAAGAGTCGTTGAAACTTAAGAC-F 5'
```

OLIGONUCLEOTIDES AND METHODS FOR THE DETECTION OF *CHLAMYDIA TRACHOMATIS*

This application is a continuation of U.S. patent application Ser. No. 08/449,863, filed Apr. 24, 1995, now abandoned which is a divisional of application Ser. No. 08/116,389, filed Sep. 3, 1993, now U.S. Pat No. 5,601,978.

FIELD OF THE INVENTION

The invention relates to oligonucleotides useful in detecting *Chlamydia trachomatis*, e.g., by the ligase chain reaction (LCR) methods.

BACKGROUND OF THE INVENTION

Microorganisms of the genus Chlamydia are obligate intracellular parasites of eukaryotic cells. They grow and multiply in the host cell forming an inclusion in the cytoplasm of the cell and cause a host of clinical syndromes.

The genus Chlamydia is made up of three distinct species: *Chlamydia psittaci*, *Chlamydia trachomatis*, and *Chlamydia pneumoniae*. Of these species, *Chlamydia trachomatis* and *Chlamydia pneumoniae* are commonly pathogenic for humans causing diseases such as conjunctivitis, trachoma genital infections, and pneumonia.

To detect *Chlamydia trachomatis*, clinical specimens are inoculated onto eukaryotic cell culture monolayers, incubated for 48 hours or more, then stained with either iodine or Giemsa. Various immunofluorescence assays are also used to detect *Chlamydia trachomatis* antigens and to detect antibodies produced in response to chlamydial infection. The use of immunofluorescence for detection of chlamydial antigens involves exposing clinical specimens suspected of containing chlamydia to fluorescein isothiocyanate (FITC) labeled monoclonal antibodies directed to chlamydial antigens.

Immunofluorescence techniques for the detection of antichlamydial antibodies include microimmunofluorescence (MIF) and indirect immunofluorescence. MIF assays are performed by fixing purified organisms to microscope slides. Both MIF and indirect immunofluorescence utilize Chlamydia as a reagent for the detection of antibodies to the organism in patient specimens. MIF utilizes purified Chlamydia fixed to a glass slide while indirect immunofluorescence utilizes Chlamydia growing in tissue culture cells as intracytoplasmic inclusions on the periphery of the nucleus of infected cells. Enzyme immunoassays are also used for the detection of Chlamydia species. All of these methods are laborious and time consuming.

Nucleic acid hybridization techniques such as dot blots, slot blots, Southern blots, solution hybridization, and in situ hybridization have been proposed as potentially useful methods for detecting a variety of pathogens including *Chlamydia trachomatis*. Polymerase chain reaction (PCR) procedures such as described in US. Pat. No. 4,683,195 to Mullis et al. have also been proposed for use in detection of a variety of pathogens.

PCT application No. WO 88/03957 published Jun. 25, 1988 by Hogan et al., addresses the detection of non-viral organisms using nucleic acid hybridization techniques. The method comprises constructing an oligonucleotide that is complementary to a region of ribosomal RNA selected to be unique to a particular non-viral organism sought to be distinguished. The Hogan application addresses oligonucleotide sequences which may be useful in the detection of *Chlamydia trachomatis* including sequences directed to 16S and 23S ribosomal RNA corresponding to sequences at bases 60–105, 175–210, 600–635, and 830–870, respectively of *E. coli* rRNA, and to sequences at bases 275–320, 330–365, 1160–1190, 1450–1490, 1510–1545, and 1710–1750, respectively of *E. coli* 23S RNA. The application also addresses probes directed to numerous other non-viral organisms.

Of additional interest to the background of the invention, is an alternate method for nucleic acid amplification known as the ligase chain reaction (LCR). In LCR, probe pairs are used which include two primary (first and second probes) and two secondary (third and fourth) probes all of which are employed in molar excess to target. The first probe hybridizes to a first segment of the target strand and the second probe hybridizes to a second segment of the target strand, the first and second segments being contiguous so that the primary probes abut one another in 5' phosphate-3' hydroxyl relationship and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes will also hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al., published Jul. 31, 1991 both of which are incorporated herein by reference.

Despite the currently available techniques, there remains a need for a sensitive, rapid, specific and reproducible technique for the detection of *Chlamydia trachomatis*.

SUMMARY OF THE INVENTION

The present invention is directed to oligonucleotide probes useful for specific detection of target DNA from *Chlamydia trachomatis*. Such an oligonucleotide probe is from 10 to about 50 nucleotides long and possesses sufficient complementarity or homology to the sequences shown in SEQ ID NOS. 1, 6, 11, 16 or 21 to hybridize with such sequence or its complement under hybridizing conditions, as defined herein. Sufficient complementarity or homology generally requires about 80% to 100% complementarity or homology. Shorter probes typically require higher percentage ranges, while longer probes typically are useful with lower percentage ranges. Preferred are probes in the range of 15 to 40, usually about 20–25 nucleotides in length. Such an oligonucleotide probe detects at least two *Chlamydia trachomatis* serovars, preferably three or more, and ideally 10 or more serovars, while not cross reacting substantially with other related organisms, including other organisms of the Chlamydia genus. Preferred examples of such oligonucleotide probes of the invention are the probes of SEQ ID NOS. 2–5, 7–10, 12–15, 17–20 and 22–25.

The present invention is also directed to compositions of two or more, preferably four, oligonucleotide probes for detecting target DNA from *Chlamydia trachomatis*, including probe set 1 (SEQ ID NOS. 2–5), probe set 2 (SEQ ID NOS. 7–10), probe set 3 (SEQ ID NOS. 12–15), probe set 4 (SEQ ID NOS. 17–20), and probe set 5 (SEQ ID NOS. 22–25) as defined herein, and combinations and subcombinations thereof.

Another aspect of the invention is a method for detecting target DNA from *Chlamydia trachomatis* comprising the steps of providing a sample suspected of containing target DNA from *Chlamydia trachomatis*, hybridizing with sample DNA an oligonucleotide probe as described above for hybridizing with one of the sequences, SEQ ID NOS. 1, 6, 11, 16 or 21, as defined herein, wherein the oligonucleotide probe is preferably labeled with a reporter group capable of directly or indirectly generating a signal, and determining the presence of target DNA by detecting hybrids, usually by detecting the signal generated by the reporter.

In another of its aspects, the present invention provides methods for amplifying and detecting target DNA from *Chlamydia trachomatis* using the ligase chain reaction (LCR) with labeled oligonucleotide probes as described above. These methods generally comprise providing a sample suspected of containing the target DNA and one or more sets of four probes according to the invention, wherein at least one probe of the probe set preferably bears a reporter group capable of detection, and performing a ligase chain reaction prior to detecting the reporter group. In an especially preferred variation of the LCR, probes are provided in modified form so that they cannot be ligated to one another prior to a target-dependent correction step. In one preferred method, modified probe sets include at least one gap which must be filled prior to ligation. Gap filling in a target-dependent manner can be accomplished by providing the appropriate deoxynucleotide triphosphate(s), but in any event less than all four deoxynucleotide triphosphates and a polymerase reagent.

The following steps are then performed at least once: mixing the probe set with the sample suspected of containing the target DNA; denaturing hybridized targets and hybridized probes; hybridizing the denatured probes to the denatured target DNA; correcting probe modifications, if present, in a template-dependent manner thereby generating adjacent probes; ligating the adjacent probes using the ligase to form reorganized probes; and detecting the label in the reorganized probes. "Correction" as used herein is used in the same sense as in EP 439,182.

Additional aspects of the invention include kits useful for the detection of *Chlamydia trachomatis*. The kits comprise one or more suitable containers containing one or more probe sets according to the present invention, a ligase reagent, and a polymerase reagent, and one or more, but not all four deoxynucleotide triphosphates. Typically, at least one probe from the probe set bears a label or reporter group, but detection is possible without this.

BRIEF DESCRIPTION OF THE FIGURES

FIG. 1 illustrates *Chlamydia trachomatis* MOMP specific target DNAs and oligonucleotide probes aligned with their respective targets.

FIG. 2 illustrates *Chlamydia trachomatis* cryptic plasmid specific target DNAs and oligonucleotide probes aligned with their respective targets.

In probe sets 1–4 of the Figures, CZ represents a carbazole derived hapten and AD represents an adamantane derived hapten. In probe set 5, B represents a biotin moiety and F represents a fluorescein moiety. These labels are described further in the text.

It should be understood that the figures and SEQ ID NOs. depict exact sequences of the probes, but that modifications or variations thereof that result in probes having similar properties (e.g. detection of *C. trachomatis* DNA) are also deemed to be within the scope and spirit of the invention.

DETAILED DESCRIPTION OF THE INVENTION

Oligonucleotide sequences (SEQ ID NOS. 1–15) (FIG. 1) of the present invention are derived from the gene coding for the major outer membrane protein (MOMP) of *Chlamydia trachomatis* as described by Baehr, W. et al., Proc. Nat'l. Acad. Sci. (USA), 85,4000–4004 (1988). The gene is at least 1120 nucleotides long and is typically present in one copy per organism. Other oligonucleotides corresponding to (SEQ ID NOS. 16–25) (FIG. 2) of the present invention were derived from a cryptic plasmid found in *Chlamydia trachomatis* (Hatt, C., et al., *Nucl. Acids Res.* 16 (9):4053–4067). The cryptic plasmid, typically present in 7–10 copies per organism, is 7498 base pairs in length and contains several open reading frames.

The modified ligase chain reaction (LCR) utilized in the present invention uses two pairs of probes herein designated A, B (primary probes), and A', B' (secondary probes). A' is substantially complementary to A, and B' is substantially complementary to B. Because of the antiparallel nature of DNA, probes A and B' are referred to herein as "upstream" probes, having their 3' end proximate their partners B and A', respectively; while probes B and A' are "downstream". At least one probe of one of the probe pairs initially includes a "modified" end which renders the hybridized probes "non-blunt" and/or not a suitable substrate for the ligase catalyzed fusion of the two probe duplexes. A "modified end" is defined with respect to the point of ligation rather than with respect to its complementary probe. Although other "modified ends" are known and within the scope of this invention, all "modified ends" described herein have omitted bases to create a "gap" between upstream and downstream probes when the probe pair is annealed to a target sequence. The presence of these modified ends reduces the falsely positive signal created by blunt-end ligation of complementary probe duplexes to one another in the absence of target.

"Correction" of the modification is subsequently carried out to render the probes ligatable. As used herein "correction" refers to the process of rendering, in a target dependent manner, the two primary probes or the two secondary probes ligatable to their partners. Thus, only those probes hybridized to target, target complement or polynucleotide sequences generated therefrom are "corrected." "Correction" can be accomplished by several procedures, depending on the type of modified end used. Correction by gap filling is exemplified herein. This utilizes a template-dependent polymerase and the requisite deoxynucleotide triphosphates (dNTPs) to extend the upstream probe until its terminus is adjacent the downstream probe. The requisite dNTP(s) is/are determined based upon the target sequence.

As used herein, "point of ligation" or "intended point of ligation" refers to a specific location between two probe partners that are to be ligated in a template-dependent manner. It is the site at which the "corrected" probe lies adjacent its partner in 3' hydroxyl-5' phosphate relationship. For each set of four LCR probes there are two "points of ligation", a point for the primary probe partners and a point for the secondary probe partners. In conventional LCR the two points of ligation are opposite one another, thus forming blunt ended duplexes when the probe pairs hybridize to one another. In the LCR method used in the embodiments of the present invention, the points of ligation are not opposite one another, but are displaced from one another by one or more bases by virtue of the gaps. The exact point(s) of ligation varies depending on the sequences chosen and, thus is further defined in the context of each embodiment.

Each of the probes comprises deoxyribonucleic acid (DNA) which may be routinely synthesized using conventional nucleotide phosphoramidite chemistry and the instruments available from Applied Biosystems, Inc., (Foster City, Calif.); DuPont, (Wilmington, Del.); or Milligen, (Bedford, Mass.). Phosphorylation of the 5' ends of the appropriate probes, while necessary for ligation by ligase, may be accomplished by a kinase or by commercial synthesis reagents, as is known in the art. It may also be desirable to utilize one or more ribonucleotide residues in a probe.

In general, the LCR methods useful in the practice of the present invention comprise denaturation, then repeated steps of (a) hybridizing the modified probes to the target (and, if double stranded so that target complement is present, to the target complement); (b) correcting the modification in a target dependent manner to render the probes ligatable; (c) ligating the corrected probe to its partner to form a fused or ligated product; and (d) dissociating the ligated product from the target and repeating the hybridization, correction and ligation steps to amplify the desired target sequence. Steps (a), (c) and (d) are essentially the same for all of the embodiments and can be discussed together. Step (b) varies depending on the type of modification employed, but only gap filling is discussed herein.

Hybridization of probes to target (and optionally to target complement) is widely known in the art and is illustrated in EP-A-320 308. Probe length, probe concentration and stringency of conditions all affect the degree and rate at which hybridization will occur. Preferably, the probes are sufficiently long to provide the desired specificity; i.e., to avoid being hybridizable to nontarget sequences in the sample. Typically, probes on the order of 15 to 100 bases serve this purpose. Presently preferred are probes having a length of about 15 to about 40 bases.

The probes are added in approximately equimolar concentration since they are expected to react stoichiometrically. Each probe is generally present in a concentration ranging from about 5 nanomolar (nM) to about 90 nM; preferably from about 10 nM to about 35 nM. For a typical reaction volume of 200 µL, this is equivalent to adding from about $1.2 \times 10^{12}$ to about $4 \times 10^{12}$ molecules of each probe; and around $2 \times 10^{12}$ molecules per 200 µL has been a good starting point, however, reaction volumes may vary. The optimum quantity of probe used for each reaction also varies depending on the number of cycles which must be performed and the reaction volume. Probe concentrations can readily be determined by one of ordinary skill in this art to provide optimum signal for a given number of cycles.

"Hybridization" or "hybridizing" conditions is defined generally as conditions which promote nucleation and annealing. It is well known in the art, however, that such annealing is dependent in a rather predictable manner on several parameters, including temperature, ionic strength, probe length and G:C content of the probes. For example, lowering the temperature of the reaction promotes annealing. For any given set of probes, melt temperature, or Tm, can be estimated by any of several known methods. Typically, diagnostic applications utilize hybridization temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased probe length are also known to stabilize duplex formation because G:C pairings involve 3 hydrogen bonds where A:T pairs have just two, and because longer probes have more hydrogen bonds holding the probes together. Thus a high G:C content and longer probe lengths impact the "hybridization conditions" by elevating the melt temperature.

Once probes are selected for a given diagnostic application, the G:C content and length will be known and can be accounted for in determining precisely what "hybridization conditions" will encompass. Since ionic strength is typically optimized for enzymatic activity, the only parameter left to vary is the temperature. For improved specificity, the hybridization temperature is selected slightly below the Tm of the probe; typically 2°–10° C. below the Tm. Thus, obtaining suitable "hybridization conditions" for a particular probe set and system is well within ordinary skill of one practicing this art.

Following provision of the probes, the next step in the LCR method utilized in the present invention is the specific correction step which creates "adjacent" probes, followed by the ligation of one probe to its adjacent partner. Thus, each corrected primary probe is ligated to its associated primary probe and each corrected secondary probe is ligated to its associated secondary probe. Correction may be accomplished using a DNA polymerase and most preferred is a thermostable DNA polymerase which obviates the need for adding additional polymerase for every cycle. The ligation of "adjacent probes" generates "reorganized probes". Since enzymatic ligation is the preferred method of covalently attaching two adjacent probes, the term "ligation" will be used throughout the application. However, "ligation" is a general term and is to be understood to include any method of covalently attaching two probes. One alternative to enzymatic ligation is photo-ligation as described in EP-A-324 616.

The conditions and reagents which make possible the preferred enzymatic ligation step are generally known to those of ordinary skill in the art. Ligating reagents useful in the present invention include T4 ligase, and prokaryotic ligases such as *E. coli* DNA ligase, and *Thermus thermophilus* DNA ligase (e.g., ATCC 27634) as taught in EP-320 308 and in EP-373 962. This latter ligase is presently preferred for its ability to maintain activity during the thermal cycling of LCR. Absent a thermally stable ligase, the ligase must be added each time the cycle is repeated. Also useful are eukaryotic ligases, including DNA ligase of Drosophila, reported by Rabin, et al., *J. BioL Chem.* 261:10637–10647 (1986).

Once ligated, the ligated (reorganized) probe is dissociated (e.g. melted) from the target and, as with conventional LCR, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation are not able themselves to participate in other unwanted ligation reactions. Thus, ligatable sticky or blunt ends should be avoided. If such ends must be used, then 5' terminal phosphates should be avoided, eliminated or blocked. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below.

It should be appreciated that the use of four probes, as described above, produces the greatest amplification since the ligated or reorganized probes themselves can serve as target-equivalent templates in further cycles, thus resulting in exponential amplification. However, it is also possible to use just two probes extended and ligated on a single strand, such as is described in U.S. Pat. No. 5,185,243, as a detection method. Repeated steps of this nature will result (in the absence of the complementary probes) in a linear amplification. One skilled in the art can easily select the appropriate probe pairs from the probe sets (e.g. probes A and B; or probes B' and A') for ligation pairs.

Following amplification, the amplified sequences can be detected by a number of conventional ways known in the art. Unlabeled probes can be detected following sepration on a gel on the basis of weight or length, and staining with a suitable dye as is known in the art. More typically, detection is performed after separation of free labeled probe from labeled ligation products, by determining the amount of label in one of the separated fractions. Separation may be accomplished by electrophoresis, by chromatography, including immunochromatography, by filtration, by the preferred specific ligand capture method described below, or by a combination of these methods.

The labeled probe(s) contains a reporter group or label that is directly or indirectly capable of detection. Direct labels include chromogens, catalysts such as enzymes, fluorescent compounds, luminescent compounds, chemiluminescent compounds, and radioactive elements such as $^{32}$P or $^3$H. Indirect labels include specific binding ligands as described below.

In a particularly preferred configuration, haptens, or "hooks" are attached as reporter groups at the available outside ends of at least two probes (opposite ends of fused product), and preferably to the outside ends of all four probes. A "hook" is any ligand or moiety having an affinity to a binding partner. Typically, the hook(s) at one end of the fused product (e.g. the 5' end of first upstream probe A and the 3' end of second downstream probe A') comprises an antigen or hapten capable of being immobilized by a specific binding reagent (such as antibody or avidin) coated onto a solid phase. The hook(s) at the other end (e.g. the 3' end of first downstream probe B and the 5' end of second upstream probe B') contains a different antigen or hapten capable of being recognized by a label or a label system such as an antibody-enzyme conjugate.

Exemplary hooks include but are not limited to haptens (such as those described below) complementary polynucleotide "tail" regions, lectin/carbohydrate pairs, enzymes and their co-factors, and others known in the art.

Many different haptens are known in the art, and virtually any hapten can be used with the present invention, provided it does not interfere with hybridization or ligation.

Some illustrative haptens include many drugs (e.g. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned patent applications U.S. Ser. No. 07/808,508 (adamantaneacetic acids) now abandoned, U.S. Ser. No. 07/808,839 in (carbazoles and dibenzofurans) now abandoned, both filed Dec. 17, 1991; U.S. Ser. No. 07/858,929 (acridines), now abandoned and U.S. Ser. No. 07/858,820 (quinolines) now abandoned, both filed Mar. 27, 1992. The entire disclosure of each of the above-mentioned previously filed hapten applications is incorporated herein by reference.

Many methods of adding haptens to probes are known in the literature. Enzo Biochemical (New York) and Clontech (Palo Alto) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. No. 625,566, filed Dec. 11, 1990 now abandoned, and U.S. Ser. No. 630,908, filed Dec. 20, 1990 now U.S. Pat. No. 5,290,925 teach methods for labeling probes at their 5' and 3' termini, respectively. Both the aforementioned copending applications are incorporated by reference.

Publications WO92/10505, published 25 Jun. 1992 and WO92/11388 published 9 Jul. 1992 teach methods for labeling probes at their 5' and 3' ends respectively. According to one known method for labeling an oligonucleotide, a label-phosphoramidite reagent is prepared and used to add the label to the oligonucleotide during its synthesis. For example, see Thuong, N. T. et al., *Tet. Letters*, 29(46): 5905–5908 (1988); or Cohen, J. S. et al., published U.S. patent application Ser. No. 07/246,688 now abandoned (NTIS ORDER No. PAT-APPL-7-246,688) (1989).

Thus, exemplary ligated oligonucleotides may have a carbazole at one end and an adamantane at the other end for the detection by the IMx® instrument (Abbott Laboratories, Abbott Park, Ill. using the microparticle enzyme immunoassay (MEIA) technology. The assay protocol is similar to that used in the commercially available alpha-fetoprotein assay, with the following adaptations: (1) the anti-alpha-fetoprotein antibody coated microparticles are replaced with anti-carbazole antibody coated microparticles; and (2) the conjugates of anti-alpha fetoprotein antibodies:alkaline phosphatase are replaced with the conjugates of anti-3-phenyl-1-adamantaneacetic acid antibodies:alkaline phosphatase.

Protocols for Microparticle Enzyme ImmunoAssays (MEIAs), such as are performed on the Abbott IMx® instrument are further described in EP-A-439,182, in EP-A-288 793 and in Fiore, M. et al *Clin. Chem.*, 34/9:1726–1732 (1988). An exemplary protocol is as follows. 100 µL of the sample which has been amplified by LCR is pipetted into the sample well. 30–50 µL of this sample is then pipetted into the incubation well, the anticarbazole antibody coated microparticles are added to the well. An appropriate period of incubation follows which allows the formation of a complex consisting of anticarbazole antibodies and nucleic acid sequences with the carbazole ends. After the incubation, the mixture is pipetted onto the glass fiber capture matrix of the IMx® reaction cell, and antiadamantane antibodies conjugated to alkaline phosphatase are added. This leads to a microparticle-oligonucleotide-enzyme complex which is captured by the glass fiber capture matrix. After the removal of excess reagent in a wash step (throughout this protocol, the blotter beneath the glass fiber capture matrix absorbs reagent solutions which would otherwise overflow the glass fiber capture matrix), the glass-fiber capture matrix is treated with 4-methylumbelliferyl phosphate (MUP). The surface-bound enzyme converts the nonfluorogenic MUP to 4-methylumbelliferone (MU), whose fluorescence can be measured. The numerical IMx rate values given in the following examples represent the rate of formation of fluorescent product, expressed in counts/sec/sec (c/s/s). The amount of ligated probe is directly related to this rate. It should be noted that the IMx® instrument typically generates "machine" noise or background in the range of 2–12 c/s/s.

In the illustrative examples which follow, probe pairs are labeled with a fluorescein hapten and a biotin hapten or with a carbazole hapten and an adamantaneacetic acid (adamantane) hapten. Typically, fluorescein and biotin are used together and adamantane and carbazole are used together in accordance with the description above although any combination of virtually any haptens would be possible. Preferably, each member of a probe pair has a different label.

Other equally suitable methods of detection useful in the practice of the present invention include ELISA, EIA, immunochromatography, and nucleic acid hybridization techniques including southern blotting, dot blotting, slot blotting, solution hybridization and others well known in the art.

Quantities of polymerase are expressed in units, defined as follows: 1 unit of enzyme equals the amount of enzyme required to incorporate 10 nanomoles total nucleotides into acid-insoluble material in 30 min at 70° C. Units of ligase enzyme are defined herein as: 1 mg of 95% purified *Thermus thermophilus* DNA ligase has a specific activity of about $1\times10^8$ units. While this is not precisely standardized and may vary by as much as 20%, optimization is within the skill of the routine practitioner.

For purposes of this invention, the target sequence is described to be single stranded. However, this should be understood to include the case where the target is actually double stranded but is simply separated from its complement prior to hybridization with the probes. In the case of double stranded target, the third and fourth (secondary) probes, A' and B', respectively, will participate in the initial step by hybridizing to the target complement. In the case of single stranded target, they will not participate in the initial hybridization step, but will participate in subsequent hybridization steps, combining with the primary fused sequence produced by ligating the first and second probes. Target sequences may comprise deoxyribonucleic acid (DNA) or ribonucleic acid (RNA), although the targets shown and claimed herein are DNA. Also for the purposes of the present invention deoxynucleotide triphosphates include: deoxyadenosine triphosphate; deoxythymidine triphosphate; deoxyguanosine triphosphate; and deoxycytosine triphosphate. However, this is not meant to exclude modified bases or nontraditional bases that are analogs of these four if they can form hydrogen bonds in an analogous manner.

The invention will now be described further by way of examples which are illustrative of the invention and are not intended to limit it in any way. For example, sequences of specific length are listed. It should be understood that sequences covering the same map positions but having slightly fewer or greater numbers of bases are deemed to be equivalents of these sequences and fall within the scope of the invention, provided they will hybridize to the same positions on the target as the listed sequences. It is also understood that sequences having homology to the target sequences of about 80% or more also fall within the scope of the present invention. Preferably any base substitutions in the LCR sequences of the present invention lie 3 or more nucleotides away from the gaps or recesses.

Because Chlamydia is an obligate intracellular parasite, it is difficult to quantify control dilutions with accuracy. Although one elementary body (EB) and one inclusion forming unit (FU) are theoretically equivalent to one organism, this equality is rarely the case in practice. When non-viable organisms are present in the same EB or IFU, the count of actual organisms is inaccurate. Control solution IFUs are estimated by their IMx rate using a standard curve calibrated against stock solutions cultured out to estimate EBs or IFUs.

EXAMPLE 1

Detection of *Chlamydia trachomatis* Using Probe Set 1 (SEQ ID NOS. 2–5)

Oligonucleotide probes were chosen to detect a target sequence corresponding to nucleotides 435–482 of the MOMP gene (SEQ ID NO. 1) of *Chlamydia trachomatis* . (FIG. 1). Probe set 1 (SEQ ID NOS. 2–5) was tested against panel of organisms consisting of a wide variety of *Chlamydia trachomatis* serovars (serological variants), for its ability to detect target DNA from these organisms. LCR reaction mixtures contained LCR buffer (50 mM EPPS, 30 mM $MgCl_2$,20 mM $K^+$[from KOH and KCl], 10 µM NAD), 1.7 µM dATP, 1.7 µM dCTP (gap-filling nucleotides) $8\times10^{11}$ molecules of each oligonucleotide probe labeled with carbazole and adamantane as described above, 5 µg/ml acetylated bovine serum albumin (BSA), 0.5 mM EDTA, 0.02% by weight sodium azide, 2 units Thermus sp. DNA polymerase (Molecular Biology Resources, Milwaukee, Wis.) 18,000 units *Thermus thermophilus* DNA ligase (Abbott Laboratories), and target DNA (equivalent to 10 elementary bodies of *Chlamydia trachomatis*), all in a total volume of 200 µl. Cycling was then performed on a Perkin-Elmer Model 480 thermocycler at the following settings: 97° C., 1 sec; 55° C., 1 sec; 62° C., 50 sec; for a total of 40 cycles.

Target DNA may be prepared by a variety of methods well known in the art. In the present example, target DNA was prepared by heating the organism (grown in McCoy cells) at 85° C.–95° C. for 10 minutes in a buffer consisting of 5 mM EPPS, 60 mM $MgCl_2$.

Following amplification, ligation products were detected using a sandwich immunoassay using an Abbott automated IMx® Analyzer as described above. Table 1 shows the results of the assay expressed as counts/sec/sec (c/s/s).

TABLE 1

| Target DNA | IMx ® Rate (c/s/s) |
|---|---|
| *C. trachomatis* serovar | |
| A | 1370 |
| B | 1076 |
| Ba | 495 |
| C | 487 |
| D | 1022 |
| E | 575 |
| F | 1140 |
| G | 527 |
| H | 458 |
| I | 640 |
| J | 724 |
| K | 1058 |
| L1 | 930 |
| L2 | 1309 |
| L3 | 1077 |
| Negative Control (330 ng salmon sperm DNA) | 14 |

These results show that probe set 1 (SEQ ID NOS 2–5) was capable of detecting target DNA from 15 different serovars of *Chlamydia trachomatis*.

EXAMPLE 2

Detection of Target DNA from Microbial Sources Using Probe Set 1 (SEQ ID NOS. 2–5)

Probe set 1 (SEQ ID NOS. 2–5) (FIG. 1) was used in LCR assays against a panel of target DNAs derived from several microbial sources. LCR was performed as described in Example 1 except that target DNA was extracted from the bacterial sources and was present in the reactions at about $10^5$ copies per reaction. Probes were labeled with carbazole and adamantane as shown in FIG. 1 as described above, and were provided at $7\times10^{11}$ molecules/200 µL reaction. The analysis was carried out in several runs on the IMx® instrument and the positive control (PC) and negative control (NC) values for each run are provided. The positive control in each run was estimated to be 5.0 IFUs of Chlamydia; the negative control was 330 ng salmon sperm DNA.

Table 2 shows the results of the assays.

TABLE 2

| Run | Target Organism | IMx® Rate (c/s/s) | PC & NC Values | |
|---|---|---|---|---|
| A | *Neisseria sicca* | 162 | PC | 1265 |
| A | *N. flavescens* | 16 | NC | 12 |
| A | *N. perflava* | 63 | | |
| A | *N. subflava* | 208 | | |
| A | *N. flava* | 20 | | |
| A | *N. catarrhalis* | 15 | | |
| B | *N. mucosa* | 76 | PC | 1254 |
| B | *N. cinerea* | 15 | NC | 12 |
| B | *N. polysacchareae* | 82 | | |
| B | *N. elongata* | 34 | | |
| B | *N. lactamica* | 51 | | |
| C | *N. gonorrhoeae* | 16 | PC | 1252 |
| C | *N. meningitidis* | 84 | NC | 66 |
| C | *Morganella morganii* | 89 | | |
| C | *Escherichia coli* | 15 | | |
| C | *Pseudomonas aeruginosa* | 15 | | |
| D | *Enterobacter aerogenes* | 15 | PC | 1283 |
| D | *Acinetobacter calcoaceticus* | 16 | NC | 12 |
| D | *Corynebacterium hoffmanni* | 26 | | |
| D | *Yersinia enterocolitica* | 14 | | |
| D | *Alcaligenes faecalis* | 115 | | |
| D | *Proteus vulgaris* | 15 | | |
| E | *Staphylococcus aureus* | 17 | PC | 1338 |
| E | *Serratia marcescens* | 36 | NC | 16 |
| E | *Staphylococcus epidermidis* | 64 | | |
| E | *Bacillus subtilis* | 16 | | |
| F | *Klebsiella pneumoniae* | 34 | PC | 1112 |
| F | *Salmonella enteritidis* | 87 | NC | 14 |
| F | *Providencia stuartii* | 15 | | |
| F | *Enterobacter cloacae* | 51 | | |
| F | *Shigella sonnei* | 15 | | |
| F | *Mima polymorpha* | 63 | | |
| G | *Hemophilus influenzae* | 16 | PC | 1266 |
| G | *Herella vagincola* | 156 | NC | 13 |
| G | *Streptococcus pyogenes* | 24 | | |
| G | *Streptococcus faecalis* | 15 | | |
| G | *Lactobacillus plantarum* | 98 | | |
| H | *Salmonella minnesota* | 16 | PC | 1238 |
| H | *Hemophilus parainfluenzae* | 49 | NC | 13 |
| H | *Aeromonas hydrophila* | 16 | | |
| H | *Corynebacterium sp.* | 14 | | |
| I | *Veillonella sp.* | 110 | PC | 1226 |
| I | *Moraxella osloensis* | 189 | NC | 14 |
| I | *Trichomonas vaginalis* | 57 | | |
| I | *Gardnerella vaginalis* | 34 | | |

The results show that probe set 1 gave relatively little detectable signal when tested with target DNA from a variety of microbial sources using LCR, when compared with the signal generated with DNA from *Chlamydia trachomatis*. Although signal from some bacterial species was greater than background, none were even ⅙ the signal from the *Chlamydia* positive control.

EXAMPLE 3

Detection of *Chlamydia trachomatis* With Probe Set 4 (SEQ ID NOS. 17–20)

Probe set 4 (SEQ ID NOS. 17, 18, 19, and 20) (FIG. 2) was used to detect a target DNA corresponding to oligonucleotides 6917–6964 (SEQ ID NO. 16) of the *Chlamydia trachomatis* cryptic plasmid described above. (FIG. 2) Reactions were performed as described in Example 1 except that the gap-filling nucleotides were dCTP and dTTP, 1.2 units of Thermus sp DNA polymerase was used and 10,800 units of *Thermus thermophilus* DNA ligase was used. Probes were provided at $6.2\times10^{11}$ molecules/200 µL reaction and cycling was performed at 97° C. for 1 sec., 55° C. for 1 sec., and 62° C. for 50 sec., for a total of 40 cycles. Ligation products were analyzed on an automated IMx® analyzer as described in Example 1 and results are shown in Table 3.

TABLE 3

| Target DNA | IMx® rate (c/s/s) |
|---|---|
| *C. trachomatis* serovar | |
| A | 988 |
| B | 871 |
| Ba | 715 |
| C | 721 |
| D | 713 |
| E | 649 |
| F | 747 |
| G | 673 |
| H | 513 |
| I | 601 |
| J | 698 |
| K | 692 |
| L1 | 693 |
| L2 | 801 |
| L3 | 839 |
| Negative Control (330 ng salmon sperm DNA) | 13 |

These results show that probe set 4 (SEQ ID NOS. 17, 18, 19, and 20) was capable of detecting target DNA from all 15 of the *Chlamydia trachomatis* serovars tested.

EXAMPLE 4

Detection of Target DNA from Intact Microorganisms Using Probe Set 4 (SEQ ID NOS. 17–20)

In order to assess the specificity of probe set 4 (SEQ ID NOS. 17–20) (FIG. 2), LCR was perform ed using a wide variety of intact microorganisms including various bacteria, fungi, and viruses as well as strains of *Chlamydia pneumoniae* and *Chlamydia psittaci*. LCR was performed as described in Example 3 except that 2 units of Thermus sp DNA polymerase and 18,000 units of *Thermus thermophilus* DNA ligase were used. The analysis was carried out in several runs on the IMx® instrument and the probe concentrations and positive control (PC) and negative control (NC) values for each run are provided in Table 5, below.

Results are shown in Tables 4 (microorganisms) and 4A (Chlamydia species).

TABLE 4

| Run | Target (Quantity) Bacterial species (organisms/reaction): | IMx® (c/s/s) |
|---|---|---|
| b | *Acinetobacter calcoaceticus* ($1.2 \times 10^7$) | 11 |
| m | *Actinomyces israelii* ($9.2 \times 10^7$) | 11 |
| b | *Aeromonas hydrophila* ($1.0 \times 10^8$) | 10 |
| b | *Alcaligenes faecalis* ($5.0 \times 10^7$) | 13 |

TABLE 4-continued

| Run | Target (Quantity)<br>Bacterial species (organisms/reaction): | IMx ® (c/s/s) |
|---|---|---|
| b | Bacillus subtilis (6.0 × 10$^7$) | 10 |
| b | Bacillus thuringiensis (3.0 × 10$^7$) | 10 |
| b | Bacteroides fragilis (2.0 × 10$^7$) | 10 |
| b | Bifidobacterium longum (1.5 × 10$^7$) | 9 |
| a | Branhamella catarrhalis (1.8 × 10$^8$) | 12 |
| c | Citrobacter freundii (3.1 × 10$^8$) | 14 |
| m | Clostridium sporogenes (7.8 × 10$^7$) | 24 |
| c | Corynebacterium renale (2.0 × 10$^8$) | 10 |
| c | Edwardsiella tarda (1.4 × 10$^8$) | 10 |
| c | Enterobacter cloacae (3.0 × 10$^7$) | 13 |
| c | Enterobacter aerogenes (1.8 × 10$^8$) | 23 |
| d | Enterococcus faecalis (6.0 × 10$^7$) | 12 |
| d | Enterococcus faecium (2.6 × 10$^8$) | 13 |
| d | Escherichia coli (8.0 × 10$^7$) | 19 |
| d | Ewingella americana (1.0 × 10$^8$) | 23 |
| d | Flavobacterium odoratum (1.0 × 10$^8$) | 12 |
| d | Fusobacterium nucleatum (2.0 × 10$^8$) | 12 |
| d | Gardnerella vaginalis (2.0 × 10$^7$) | 24 |
| d | Hafnia alvei (6.0 × 10$^8$) | 17 |
| n | Helicobacter pylori (1.0 × 10$^5$) | 11 |
| e | Hemophilus influenzae (3.0 × 10$^7$) | 15 |
| l | Hemophilus ducreyi (3.0 × 10$^6$) | 11 |
| e | Klebsiella pneumoniae (7.0 × 10$^7$) | 11 |
| e | Lactobacillus casei (1.0 × 10$^8$) | 9 |
| e | Morganella morganii (3.0 × 10$^7$) | 12 |
| l | Moraxella lacunata (3.4 × 10$^7$) | 11 |
| l | Mycobacterium tuberculosis RaH37 (1.0 × 10$^7$) | 27 |
| a | Mycobacterium avium (4.0 × 10$^9$) | 10 |
| a | Mycobacterium gordonae (5.0 × 10$^8$) | 11 |
| e | Neisseria gonorrheae (4.0 × 10$^7$) | 11 |
| e | Neisseria lactamica (3.0 × 10$^7$) | 16 |
| e | Neisseria meningitidis (2.0 × 10$^7$) | 10 |
| e | Neisseria sicca (2.0 × 10$^7$) | 10 |
| f | Pasteurella multocida (1.0 × 10$^8$) | 18 |
| f | Peptostrept. asaccharolyticus (2.0 × 10$^7$) | 14 |
| f | Pleisiomonas shigelloides (7.0 × 10$^7$) | 16 |
| f | Proteus mirabilis (4.0 × 10$^7$) | 17 |
| f | Proteus vulgaris (3.0 × 10$^8$) | 17 |
| f | Propionibacterium acnes (2.0 × 10$^7$) | 11 |
| f | Providencia stuartii (2.8 × 10$^8$) | 10 |
| f | Pseudomonas aeruginosa (8.0 × 10$^8$) | 15 |
| g | Salmonella enteritidis (2.7 × 10$^8$) | 22 |
| g | Salmonella minnesota (7.0 × 10$^7$) | 20 |
| g | Salmonella typhimurium (4.0 × 10$^7$) | 19 |
| g | Shigella sonnei (2.0 × 10$^8$) | 23 |
| o | Staphylococcus aureus ATCC6358 (1.0 × 10$^7$) | 127 |
| g | Staphylococcus epidermidis (2.5 × 10$^8$) | 14 |
| l | Streptococcus agalactiae (1.2 × 10$^7$) | 10 |
| g | Streptococcus mitis (1.3 × 10$^8$) | 12 |
| h | Streptococcus mutans (1.1 × 10$^8$) | 10 |
| h | Streptococcus pneumoniae (6.0 × 10$^7$) | 9 |
| h | Streptococcus pyogenes (9.0 × 10$^7$) | 21 |
| l | Streptomyces griseus (5.1 × 10$^7$) | 14 |
| h | Veillonella caviae (3.0 × 10$^7$) | 10 |
| h | Vibrio parahemolyticus (5.7 × 10$^8$) | 10 |
| h | Yersinia enterocoliticus (4.0 × 10$^8$) | 23 |
| Yeast and Fungi species: | | |
| l | Blastomyces dermatidis (DNA, 0.5 ug) | 10 |
| b | Candida albicans (9.0 × 10$^7$) | 9 |
| c | Candida albicans (4.0 × 10$^7$) | 10 |
| c | Cryptococcus laurentii (7.0 × 10$^7$) | 4 |
| l | Cryptococcus neoformans (DNA, 0.5 ug) | 10 |
| l | Histoplasma capsulatum (DNA, 0.5 ug) | 18 |
| g | Saccharomyces cerevisiae (9.0 × 10$^7$) | 13 |
| Viruses: | | |
| i | Adenovirus (1.0 × 10$^5$) | 11 |
| k | Cytomegalovirus 169 (1.0 × 10$^5$) | 105 |
| k | Epstein-Barr virus (1.0 × 10$^5$) | 10 |
| k | Hepatitis A & B virus (1.0 × 10$^5$) | 90 |
| i | Herpes simplex virus I (1.0 × 10$^5$) | 12 |
| i | Herpes simplex virus II (1.0 × 10$^5$) | 12 |
| k | Human herpes virus 6 (1.0 × 10$^5$) | 10 |
| i | HIV provirus (1.0 × 10$^5$) | 12 |
| i | Human papilloma virus 16 (1.0 × 10$^5$) | 11 |

TABLE 4-continued

| Run | Target (Quantity)<br>Bacterial species (organisms/reaction): | IMx ® (c/s/s) |
|---|---|---|
| j | Human papilloma virus 18 (1.0 × 10$^5$) | 21 |
| k | Varicella zoster (1.0 × 10$^5$) | 10 |
| Parasites: | | |
| i | Treponema pallidum (DNA, 1.0 × 10$^5$) | 11 |

TABLE 4A

| Run | Target | IMx ® Rate (c/s/s) | Result |
|---|---|---|---|
| | Chlamydia pneumoniae strains: | | |
| p | TWR 183 | 14 | (−) |
| p | AR 39 | 10 | (−) |
| p | AR 388 | 9 | (−) |
| p | CM 1 | 20 | (−) |
| p | CWL011 | 13 | (−) |
| q | BAL 15 | 98 | (−) |
| q | BAL 16 | 10 | (−) |
| q | BAL 37 | 10 | (−) |
| q | FM 16 | 16 | (−) |
| r | VR 1310 | 14 | (−) |
| r | VR 1356 (2023) | 192 | (−) |
| r | VR 1355 (2043) | 95 | (−) |
| r | 2364 | 13 | (−) |
| | Chlamydia psittaci strains: | | |
| p | SM006 | 15 | (−) |
| p | 6BC | 12 | (−) |

The probe concentrations used and the resulting positive control (PC) and negative control (NC) values for each run of Example 4 are given in Table 5. The positive control was estimated to be 5.0 IFUs of *Chlamydia trachomatis* and the negative control was 330 ng salmon sperm DNA in each run.

TABLE 5

| Run | Probe Concentration | PC Value | NC Value |
|---|---|---|---|
| a | 6.0 × 10$^{11}$ molecules/reaction | 1704 | 10 |
| b | 6.0 × 10$^{11}$ molecules/reaction | 1436 | 9 |
| c | 6.0 × 10$^{11}$ molecules/reaction | 1514 | 9 |
| d | 6.0 × 10$^{11}$ molecules/reaction | 1246 | 11 |
| e | 6.0 × 10$^{11}$ molecules/reaction | 1024 | 9 |
| f | 6.0 × 10$^{11}$ molecules/reaction | 1166 | 9 |
| g | 6.0 × 10$^{11}$ molecules/reaction | 1970 | 12 |
| h | 6.0 × 10$^{11}$ molecules/reaction | 1323 | 9 |
| i | 6.0 × 10$^{11}$ molecules/reaction | 1401 | 10 |
| j | 6.0 × 10$^{11}$ molecules/reaction | 1409 | 11 |
| k | 6.0 × 10$^{11}$ molecules/reaction | 1223 | 9 |
| l | 4.6 × 10$^{11}$ molecules/reaction | 1756 | 10 |
| m | 4.6 × 10$^{11}$ molecules/reaction | 1412 | 10 |
| n | 6.0 × 10$^{11}$ molecules/reaction | 1223 | 9 |
| o | 5.0 × 10$^{11}$ molecules/reaction | 1951 | 11 |
| p | 5.0 × 10$^{11}$ molecules/reaction | 1575 | 10 |
| q | 5.0 × 10$^{11}$ molecules/reaction | 1851 | 10 |
| r | 5.0 × 10$^{11}$ molecules/reaction | 1888 | 10 |

These results show that probe set 4 (SEQ ID NOS. 17, 18, 19, and 20) produced ligation products only when *Chlamydia trachomatis* was present in the LCR reaction mixture and not when a wide variety of other microorganisms were present, including closely related *Chlamydia pneumoniae* and *Chlamydia psittaci* strains.

EXAMPLE 5

Detection of *Chlamydia trachomatis* With Probe Set 5 (SEQ ID NOS. 22–25)

Probe set 5 (SEQ ID NOS. 22–25) (FIG. 2) was used to detect a target DNA corresponding to nucleotides 6107–6160 (SEQ ID NO. 21) (FIG. 2) of the *Chlamydia trachomatis* cryptic plasmid described above. Reactions were conducted as described in Example 1 also using gap-filling nucleotides dATP and DCTP, but not acetylated BSA. Cycling was performed at 97° C. for 1 sec., 58° C. for 1 sec., and 65° C. for 20 secs. for a total of 37 cycles. Probes were labeled with biotin and fluorescein as described above, and provided at $2 \times 10^{12}$ molecules/200 µL reaction. Ligation products were analyzed on an IMx® analyzer as shown in FIG. 2 and as described above. Results are shown in Table 6.

TABLE 6

| Target DNA | IMx ® Rate (c/s/s) |
|---|---|
| *C. trachomatis* serovar | |
| A | 916 |
| B | 864 |
| Ba | 833 |
| C | 894 |
| D | 741 |
| E | 557 |
| F | 796 |
| G | 909 |
| H | 697 |
| I | 598 |
| J | 870 |
| K | 772 |
| L1 | 1211 |
| L2 | 1387 |
| L3 | 1390 |
| Negative Control (330 ng Human Placental DNA) | 86 |

These results show that probe set 5 (SEQ ID NOS. 22–25) is capable of detecting 15 different serovars of *Chlamydia trachomatis*.

EXAMPLE 6
Detection of Target DNA from Microbial Sources Using Probe Set 5 (SEQ ID NOS. 22–25)

The specificity of probe set 5 was assessed using target DNA from a series of non-chlamydial microorganisms. LCR was performed as described in Example 5 in four runs except that target DNA was present at about $10^5$ genomes/reaction. Positive Control (PC) was estimated to be 5.0 IFUs and Negative Control (NC) was 330 ng human placental DNA in each run. The PC and NC values for each run are shown in Table 7. IMx® analysis was performed as described above. Table 7 also shows the results of these assays.

TABLE 7

| Run | Organism | IMx ® Rate (c/s/s) | PC & NC Values | |
|---|---|---|---|---|
| A | Lactobacillus | 16 | PC | 2148 |
| A | *Hemophilus ducreyi* | 21 | NC | 11 |
| A | Fusobacterium | 43 | | |
| A | Yersinia | 10 | | |
| A | Corynebacterium | 18 | | |
| B | *Hemophilus influenzae* | 28 | PC | 2228 |
| B | *Bacillus fragilis* | 21 | NC | 22 |
| B | *Candida albicans* | 23 | | |
| B | *Klebsiella pneumoniae* | 29 | | |
| B | *Gardnerella vaginalis* | 26 | | |
| B | *Staphylococcus epidermidis* | 42 | | |
| C | Acinetobacter | 28 | PC | 2018 |
| C | *Streptococcus faecalis* | 9 | NC | 17 |
| C | Pseudomonas | 20 | | |
| C | *Proteus vulgaris* | 10 | | |
| C | *Chlamydia psittaci* | 11 | | |

TABLE 7-continued

| Run | Organism | IMx ® Rate (c/s/s) | PC & NC Values | |
|---|---|---|---|---|
| C | *Escherichia coli* | 9 | | |
| C | *Neisseria gonorrhoeae* | 14 | | |
| D | *Neisseria meningitidis* | 11 | PC | 2120 |
| | | | NC | 21 |

These results indicate that probe set 5 (SEQ ID NOS. 22–25) shows no cross reactivity with target DNA derived from a variety of non-chlamydial microorganisms or from *Chlamydia psittici*.

EXAMPLE 7
Detection of *Chlamydia trachomatis* Target DNA Using Probe Set 2 (SEQ ID NOS. 7–10)

Probe set 2 (SEQ ID NOS. 7–10) was used to detect target DNA corresponding to nucleotides 788–835 (SEQ ID NO. 6) of the MOMP gene of *Chlamydia trachomatis*. (FIG. 1). Probes were synthesized and labeled as shown in FIG. 1 and described above, and were provided at $2 \times 10^{12}$ molecules/200 µL reaction.

LCR assays were performed as described in Example 1 using dATP and dCTP as gap filling nucleotides. Table 8 shows the results of the assays.

TABLE 8

| Target DNA | IMx ® Rate (c/s/s) |
|---|---|
| *C. trachomatis* Serovar | |
| A | 11 |
| B | 32 |
| Ba | 21 |
| C | 24 |
| D | 182 |
| E | 11 |
| F | 232 |
| G | 83 |
| H | 26 |
| I | 9 |
| J | 11 |
| K | 44 |
| L1 | 220 |
| L2 | 218 |
| L3 | 9 |
| Negative Control (330 ng human placental DNA) | 30 |

These results show that probe set 2 yielded relatively low IMx® rates in most serovars tested. The best results were obtained for serovars D, F, L1, and L2.

EXAMPLE 8
Detection of Non-Chlamydia Target DNA Using Probe Set 2 (SEQ ID NOS. 7–10)

Probe set 2 was used at $2 \times 10^{12}$ molecules/200 µL reaction in LCR assays using target DNAs from a variety of non-chlamydial microorganisms. LCR was performed as described in Example 7 except that target DNA was present at about $10^8$ genomes per reaction. Positive Control (PC) was estimated to be 5.0 IFUs and Negative Control (NC) was 330 ng human placental DNA in each run. Results of these assays are shown in Table 9.

TABLE 9

| Run | Organism | IMx ® Rate (c/s/s) | PC & NC Values | |
|---|---|---|---|---|
| a | *Neisseria sicca* | 15 | PC | 687 |
| a | *Neisseria flavescens* | 12 | NC | 14 |
| a | *Neisseria perflava* | 11 | | |
| a | *Neisseria subflava* | 11 | | |
| a | *Neisseria flava* | 10 | | |
| a | *Neisseria catarrhalis* | 10 | | |
| b | *Neisseria mucosa* | 11 | PC | 640 |
| b | *Neisseria cinerea* | 11 | NC | 13 |
| b | *Neisseria polysacchareae* | 11 | | |
| b | *Neisseria elongata* | 11 | | |
| b | *Neisseria lactamica* | 11 | | |
| c | *Neisseria meningitidis* | 13 | PC | 675 |
| c | *Neisseria gonorrhoeae* | 17 | NC | 15 |
| c | *Moraxella morganii* | 12 | | |
| c | *Escherichia coli* | 11 | | |
| c | *Pseudomonas aeruginosa* | 11 | | |
| d | *Enterobacter aerogenes* | 13 | PC | 680 |
| d | *Acinetobacter calcoaceticus* | 12 | NC | 13 |
| d | *Yersinia enterocoliticus* | 10 | | |
| d | *Alcaligenes faecalis* | 10 | | |
| d | *Proteus vulgaris* | 10 | | |

These results show that probe set 2 did not produce detectable ligation products when DNA from a variety of non-chlamydial bacteria were used as target DNA.

EXAMPLE 9
Detection of *Chlamydia trachomatis* Using Probe Set 3 (SEQ ID NOS. 12–15)

Probe set 3 (SEQ ID NOS. 12–15) was assessed for its ability to detect target DNA corresponding to nucleotides 1501–1506 of the MOMP gene in a variety of serovars of *Chlamydia trachomatis*. (FIG. 1). LCR was performed as described in Example 1 (using dATP and dCTP as filling nucleotides) except that cycling was performed as follows: 97° C., 1 sec; 58° C., 1 sec; 65° C., 10 sec; for a total of 37 cycles. Probes were used at $2 \times 10^{12}$ molecules/200 µL reaction. Results are shown in Table 10.

TABLE 10

| Target DNA | IMx ® Rate (c/s/s) |
|---|---|
| *C. trachomatis* Serovar | |
| A | 32 |
| B | 317 |
| Ba | 209 |
| C | 54 |
| D | 360 |
| E | 141 |
| F | 190 |
| G | 272 |
| H | 122 |
| I | 10 |
| J | 336 |
| K | 27 |
| L1 | 290 |
| L2 | 356 |
| L3 | 286 |
| Negative Control (330 ng human placental DNA) | 11 |

The results show that probe set 3 (SEQ ID NOS. 12–15) was capable of detecting target DNA from *Chlamydia trachomatis* serovars B, Ba, D, E, F, G, H, J, L1, L2 and L3, while target DNA from serovars A, C, I and K yielded little signal.

The forgoing examples are presented by way of illustration and are not intended to limit the scope of the invention as set forth in the appended claims. For example, sequences of specific length are listed. It should be understood that sequences covering the same map positions but having fewer or greater numbers of nucleotides are deemed to be equivalents of these sequences and fall within the scope of the invention, provided they will hybridize to the same positions on the target as the listed sequences.

---

We claim:

1. A composition for detecting target DNA from *Chlamydia trachomatis*, said composition comprising probe set 4 (SEQ ID NOS. 17–20).

2. A method for detecting the presence of target DNA from *Chlamydia trachomatis* in a sample, said method utilizing a ligase chain reaction comprising the steps of:
   a) mixing together a sample suspected of containing said target DNA, and probe set 4 (SEQ ID NOS. 17–20);
   b) providing one or more, but less than all four deoxynucleotide triphosphates, a polymerase, and a ligase;
   c) denaturing said mixture of sample and probe set to separate double stranded DNA;
   d) hybridizing said probe set to the denatured DNA thereby creating hybridized probes having a gap between each probe of each probe pair;
   e) correcting said hybridized probes in a template-dependent manner thereby creating adjacent and ligatable probes;
   f) ligating said adjacent probes to form reorganized probes;
   g) repeating steps b) through f) at least once; and
   h) determining the extent of formation of reorganized probes as a measure of the presence of target DNA from *Chlamydia trachomatis*.

3. A kit useful in detecting target DNA from *Chlamydia trachomatis*, said kit comprising one or more suitable containers containing:
   a) one set of four oligonucleotide probes wherein said probe set is probe set 4 (SEQ ID NOS. 17–20).

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Chlamydia trachomatis ( x i ) SEQUENCE DESCRIPTION: SEQ ID NO:1:

GCTTTGAGTT CTGCTTCCTC CTTGCAAGCT CTGCCTGTGG GGAATCCT      48

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GCTTTGAGTT CTGCTTCCTC CTTG    24

( 2 ) INFORMATION FOR SEQ ID NO:3:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:3:

GGAGGAAGCA GAACTCAAAG C    21

( 2 ) INFORMATION FOR SEQ ID NO:4:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:4:

GCTCTGCCTG TGGGGAATCC T    21

( 2 ) INFORMATION FOR SEQ ID NO:5:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:5:

AGGATTGCCC ACAGGCAGAG CTTG    24

( 2 ) INFORMATION FOR SEQ ID NO:6:

( i ) SEQUENCE CHARACTERISTICS:
      ( A ) LENGTH: 48 base pairs
      ( B ) TYPE: nucleic acid
      ( C ) STRANDEDNESS: double
      ( D ) TOPOLOGY: linear ( i i ) MOLECULE TYPE: DNA (genomic)

( v i ) ORIGINAL SOURCE:
      ( A ) ORGANISM: Chlamydia trachomatis ( x i ) SEQUENCE DESCRIPTION: SEQ ID NO:6:

TTGGGATCGT TTTGATGTAT TCTGTACATT AGGAGCCACC AGTGGATA    48

( 2 ) INFORMATION FOR SEQ ID NO:7:

( i ) SEQUENCE CHARACTERISTICS:
      ( A ) LENGTH: 25 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:7:

TTGGGATCGT TTTGATGTAT TCTGT    25

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GAATACATCA AAACGATCCC AA    22

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTAGGAGCCA CCAGTGGATA    20

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

TATCCACTGG TGGCTCCTAA TGT    23

( 2 ) INFORMATION FOR SEQ ID NO:11:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Chlamydia trachomatis ( x i ) SEQUENCE DESCRIPTION: SEQ ID NO:11:

TGGATGCAGA CAAATACGCA GTTACAGTTG AGACTCGCTT GATCGA    46

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

TGGATGCAGA CAAATACGCA GTT 23

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

TGCGTATTTG TCTGCATCCA 20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:14:

GTTGAGACTC GCTTGATCGA 20

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:15:

TCGATCAAGC GAGTCTCAAC TGT 23

( 2 ) INFORMATION FOR SEQ ID NO:16:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (extrachromosomal)

( v i ) ORIGINAL SOURCE:
        ( A ) ORGANISM: Chlamydia trachomatis ( x i ) SEQUENCE DESCRIPTION: SEQ ID NO:16:

GACTTTGCAA CTCTTGGTGG TAGACTTGGT CATAATGGAC TTTTGTTG 48

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:17:

GACTTTGCAA CTCTTGGTGG TAGA 24

( 2 ) INFORMATION FOR SEQ ID NO:18:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:18:

ACCACCAAGA GTTGCAAAGT C                   21

( 2 ) INFORMATION FOR SEQ ID NO:19:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:19:

GGTCATAATG GACTTTTGTT G                   21

( 2 ) INFORMATION FOR SEQ ID NO:20:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear ( i i ) MOLECULE TYPE: DNA (synthetic)

( x i ) SEQUENCE DESCRIPTION: SEQ ID NO:20:

CAACAAAAGT CCATTATGAC CAAG                24

( 2 ) INFORMATION FOR SEQ ID NO:21:

( i ) SEQUENCE CHARACTERISTICS:
      ( A ) LENGTH: 54 base pairs
      ( B ) TYPE: nucleic acid
      ( C ) STRANDEDNESS: double
      ( D ) TOPOLOGY: linear ( i i ) MOLECULE TYPE: DNA (extrachromosomal)

( v i ) ORIGINAL SOURCE:
      ( A ) ORGANISM: Chlamydia trachomatis ( x i ) SEQUENCE DESCRIPTION: SEQ ID NO:21:

ATTTTAAGAA GACGCTTCCT TCCATTGAAC TATTCTCAGC AACTTTGAAT TCTG        54

( 2 ) INFORMATION FOR SEQ ID NO:22:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: DNA (synthetic)

( x i ) SEQUENCE DESCRIPTION: SEQ ID NO:22:

ATTTTAAGAA GACGCTTCCT TCCATTG             27

( 2 ) INFORMATION FOR SEQ ID NO:23:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:23:

TGGAAGGAAG CGTCTTCTTA AAAT     24

( 2 ) INFORMATION FOR SEQ ID NO:24:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: circular ( i i ) MOLECULE TYPE: DNA (synthetic)

( x i ) SEQUENCE DESCRIPTION: SEQ ID NO:24:

TATTCTCAGC AACTTTGAAT TCTG     24

( 2 ) INFORMATION FOR SEQ ID NO:25:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:25:

CAGAATTCAA AGTTGCTGAG AATAGTT     27